United States Patent
Wang

(10) Patent No.: US 11,357,814 B2
(45) Date of Patent: Jun. 14, 2022

(54) **APPLICATION OF *SARCOCOCCA VAGANS*, CHINESE MEDICINAL OINTMENT FOR TREATING SKIN DISEASE, PREPARATION METHOD AND APPLICATION THEREOF**

(71) Applicant: Zhiyong Wang, Henan (CN)

(72) Inventor: Zhiyong Wang, Henan (CN)

( * ) Notice: Subject to any disclaimer, the term of this patent is extended or adjusted under 35 U.S.C. 154(b) by 343 days.

(21) Appl. No.: 16/479,742

(22) PCT Filed: Jul. 12, 2017

(86) PCT No.: PCT/CN2017/092668
§ 371 (c)(1),
(2) Date: Jul. 22, 2019

(87) PCT Pub. No.: WO2018/137319
PCT Pub. Date: Aug. 2, 2018

(65) Prior Publication Data
US 2021/0353702 A1  Nov. 18, 2021

(30) Foreign Application Priority Data
Jan. 24, 2017  (CN) .......................... 201710054418.4

(51) Int. Cl.
A61K 36/534 (2006.01)
A61K 9/00 (2006.01)
A61K 36/185 (2006.01)

(52) U.S. Cl.
CPC .......... *A61K 36/534* (2013.01); *A61K 9/0014* (2013.01); *A61K 36/185* (2013.01); *A61K 2236/15* (2013.01); *A61K 2236/331* (2013.01); *A61K 2236/51* (2013.01)

(58) Field of Classification Search
None
See application file for complete search history.

(56) References Cited

FOREIGN PATENT DOCUMENTS

| CN | 1146353 A | * | 4/1997 |
| CN | 105727227 A | | 7/2006 |
| CN | 106727925 A | | 5/2017 |

OTHER PUBLICATIONS

Khan (Isolation and Characterization of a New Compound from Sarcococca saligna, IJSR: 2319-7064, 2013). (Year: 2013).*
International Search Report dated Oct. 12, 2017 for corresponding PCT application No. PCT/CN2017/092668.
Zhang,Yiyun et al., "Parmacodynamics Study in Li Medicine Plants Sarcococca vagans Stapf," Chinese Journal of Ethnomedicine and Ethnopharmacy, vol. 26, No. 5, p. 46 et.seq. (Mar. 2017) [English Abstract, and with a machine-generated English translation of p. 46, para. 1].
Kang, Jian, Study on Resource and Application of Wild Medicinal Plants in the Miao Nationality Resident Regions in the West of Hu'nan Province, Journal of Medicine & Pharmacy of Chinese Minorities, No. 7, pp. 36-39 (2007) [English Abstract at end of article, and with a machine-generated translation of Table 1 on p. 37].
He, Kang et al., "Advance on the Chemical and Pharmacological Studies on Plants of Sarcococca," Journal of Medicine & Pharmacy of Chinese Minorities, No. 7, pp. 71-73 (2007) [with a machine-generated English translation].
Chen, Fei et al., "Research on Screening of Effective Antiviral Parts of Mentha Haplocalyx," Shandong Journal of Traditional Chinese Medicine, vol. 34, No. 4, pp. 289-291 (Apr. 2015) [English Abstract].
Written Opinion of the International Search Authority dated Oct. 12, 2017 for corresponding PCT application No. PCT/CN2017/092668 (English Translation).
Kang, Jian, "Study on Resource and Application of Wild Medicinal Plants in the Miao Nationality Resident Regions in the West of Hu'nan Province," Journal of Medicine & Pharmacy of Chinese Minorities, No. 7, pp. 36-39 (2007) [English Abstract at end of article and with machine-generated translation of Table 1 on p. 37].

* cited by examiner

*Primary Examiner* — Susan Hoffman
*Assistant Examiner* — Jacob A Boeckelman
(74) *Attorney, Agent, or Firm* — Abelman, Frayne & Schwab

(57) ABSTRACT

A Chinese medicinal ointment capable of diminishing inflammation, reducing swelling, clearing heat, and removing dampness and being used to treat a skin disease and a preparation method and application thereof. The Chinese medicinal ointment is made of 10-30 parts by weight of *Sarcococca vagans* and 1-5 parts by weight of mint. Also provided is an application of *Sarcococca vagans* in preparing a drug for diminishing inflammation and reducing swelling.

14 Claims, No Drawings

APPLICATION OF *SARCOCOCCA VAGANS*, CHINESE MEDICINAL OINTMENT FOR TREATING SKIN DISEASE, PREPARATION METHOD AND APPLICATION THEREOF

CROSS-REFERENCE TO RELATED APPLICATION

The present disclosure claims the priority to the Chinese patent application with the filing number CN201710054418.4 filed on Jan. 24, 2017 with the Chinese Patent Office, and entitled "Chinese Medicinal Ointment for Treating Skin Disease, Preparation Method and Application thereof", the contents of which are incorporated herein by reference in entirety.

TECHNICAL FIELD

The present disclosure relates to the technical field of Chinese herbal medicines, in particular to an application of *Sarcococca vagans* (*Sarcococca vagans* Stapf), a Chinese medicinal ointment for treating skin disease, a preparation method and application thereof.

BACKGROUND ART

As a first physiological defense and the biggest organ of human body, the skin constantly takes part in functional activities of the body, maintains the body's health, acts as a barrier, and functions to feel, regulate body temperature, absorb, secrete, excrete and so on. To be specific, the skin covers the whole body, so as to protect various tissues and organs in the body against physical, mechanical, chemical and pathogenic microorganic invasion; the skin is a sense organ of the human body, and it continuously feels various changes taking place in vitro; the skin is also a thermostat of the human body. On one hand, when the temperature is too high, the skin dissipates heat by increasing perspiration, and on the other hand, when an external temperature is too low, skin vessels constrict to reduce perspiration, maintaining the stability of body temperature; the skin further has functions of moisturizing hair, discharging waste and absorption. Besides, abnormalities of the body also can be reflected from skin surface.

Skin disease is a general name of diseases occurring to skin and skin appendant organ. As to the skin diseases, after the skin is affected by internal and external factors, the skin's morphology, structure and function are all changed, generating a pathological process, and correspondingly creating various clinical manifestations in succession. The skin diseases, with very high morbidity, are quite common, and are not easy to eradicate, but relapse, causing huge physical and mental pains to patients and affecting living quality. In recent years, due to influence of factors such as aggravated environment pollution and increased pressure caused by accelerated pace of life, the morbidity of skin diseases continuously rises.

Administration routes for medication of skin diseases include external use, oral administration, injection and other manners. Since an externally used drug can directly contact an injured part of the skin, it can exert better effect, and have good therapeutic effect, thus being popular among doctors and patients.

At present, externally used skin drugs commonly used by skin patients, for example, Fluocinolone acetonide, Clobetasole propionate oint., and Ketoconazole, all contain hormone, and long-term use of these drugs will cause elevated blood sugar, lowered serum potassium, infection, obesity and so on, meanwhile, abruptly stopping the medication further will cause relapse.

*Sarcococca vagans* Stapf, also called as *Sarcococca vagans*, belongs to *sarcococca* plants of boxwood family. No research of *Sarcococca vagans* Stapf in medicines has been reported yet.

In view of this, the present disclosure provides a Chinese medicinal ointment for treating skin disease with a high cure rate, no side effects, and no liability to relapse, a preparation method and application thereof.

SUMMARY

An object of the present disclosure is to provide a Chinese medicinal ointment for treating skin disease. Through scientific compatibility of *Sarcococca vagans* Stapf and mint, the Chinese medicinal ointment addresses both symptoms and root causes, with simple raw materials, has efficacies of diminishing inflammation, reducing swelling, clearing heat and removing dampness, can effectively treat skin diseases, and has advantages of a short treatment cycle, a high cure rate, no toxic or side effects and no liability to relapse.

A second object of the present disclosure is to provide a preparation method for the above Chinese medicinal ointment for treating skin disease. The preparation method is simple in operation, and can retain medical efficacies of various medicinal materials to the greatest extent without special equipment.

A third object of the present disclosure is to provide an application of the above Chinese medicinal ointment for treating skin disease, which is applicable to viral skin diseases, allergic skin diseases, fungal skin diseases, physical skin diseases and so on.

A fourth object of the present disclosure is to provide an application of *Sarcococca vagans* Stapf in preparation of a drug for diminishing inflammation and reducing swelling.

In order to achieve the above objects, technical solutions used in the present disclosure are as follows:

A Chinese medicinal ointment for treating skin disease, wherein the Chinese medicinal ointment consists of a Chinese herb extract and an ointment matrix, and wherein the Chinese herb extract is prepared from following raw materials in part by weight: 10-30 parts of *Sarcococca vagans* Stapf and 1-5 parts of mint.

Further, the Chinese herb extract is prepared from following raw materials in part by weight: 12-28 parts of the *Sarcococca vagans* Stapf and 2-4 parts of the mint.

Further, the Chinese herb extract is prepared from following raw materials in part by weight: 15-25 parts of the *Sarcococca vagans* Stapf and 2-4 parts of the mint.

Further, the Chinese herb extract is prepared from following raw materials in part by weight: 15 parts of the *Sarcococca vagans* Stapf and 2 parts of the mint.

Further, the Chinese herb extract is prepared from following raw materials in part by weight: 20 parts of the *Sarcococca vagans* Stapf and 3 parts of the mint leaf.

Further, the Chinese herb extract is prepared from following raw materials in part by weight: 30 parts of the *Sarcococca vagans* Stapf and 5 parts of the mint.

Further, the *Sarcococca vagans* Stapf is roots of dried *Sarcococca vagans* Stapf.

Further, the ointment matrix is Vaseline® petroleum jelly or polyethylene glycol.

More further, a weight ratio of the Chinese herb extract to the ointment matrix is 1:1-5.

The present disclosure further provides a preparation method for the above Chinese medicinal ointment for treating skin disease, including following steps:

(1) preparing a Chinese herb extract, which comprises: weighing *Sarcococca vagans* Stapf and mint according to part by weight, decocting them in water, and after still standing, taking and concentrating a supernatant, to obtain the Chinese herb extract; and (2) preparing an ointment, which comprises: mixing the Chinese herb extract obtained in step (1) with an ointment matrix, and stirring them evenly to prepare the ointment.

Further, the amount of water added in the step (1) is 12-18 times the weight of crude drugs.

Further, the *Sarcococca vagans* Stapf and the mint are first cut into slices before being decocted in water.

Further, after water is added, the *Sarcococca vagans* Stapf and the mint are decocted after being immerged in water for 2-4 hours.

Further, the decocting lasts for 30-60 minutes in the step (1).

More further, the *Sarcococca vagans* Stapf and the mint are in still standing for 4-8 hours after being decocted in water, and then a supernatant is taken.

The present disclosure further provides an application of the above Chinese medicinal ointment for treating skin disease, wherein the skin disease includes viral skin diseases, allergic skin diseases, fungal skin diseases and physical skin diseases.

The present disclosure further provides an application of *Sarcococca vagans* Stapf in preparation of a drug for diminishing inflammation and reducing swelling.

Compared with the prior art, beneficial effects of the present disclosure lie in:

1. *Sarcococca vagans* Stapf and mint are taken as crude drugs of the Chinese medicinal ointment provided in the present disclosure, in particular, it is found in the present disclosure that *Sarcococca vagans* Stapf has the effects of diminishing inflammation and reducing swelling, and compatibility of the two drugs has the efficacies of diminishing inflammation, reducing swelling, clearing heat and removing dampness, can effectively treat skin diseases, and has the advantages of a short treatment cycle, a high cure rate, no toxic or side effects and no liability to relapse.

2. The preparation method for the Chinese medicinal ointment provided in the present disclosure is simple in operation, can retain medical efficacies of various medicinal materials to the greatest extent without special equipment, and can be used for large-scale manufacture.

3. The Chinese medicinal ointment provided in the present disclosure is applied to a wide scope, and can treat various kinds of skin diseases, such as viral skin diseases, allergic skin diseases, fungal skin diseases and physical skin diseases.

4. The application of *Sarcococca vagans* Stapf in preparing a drug for diminishing inflammation and reducing swelling provided in the present disclosure expands the usage range of *Sarcococca vagans* Stapf, and provides basis for application of *Sarcococca vagans* Stapf.

DETAILED DESCRIPTION OF EMBODIMENTS

Technical solutions of the present disclosure will be described below clearly and completely in connection with examples. Apparently, the described examples are only a part of examples of the present disclosure, rather than all examples. All other examples, obtained by those ordinarily skilled in the art based on the examples of the present disclosure without using any inventive efforts, shall fall into the scope of protection of the present disclosure.

A Chinese medicinal ointment for treating skin disease, wherein the Chinese medicinal ointment consists of a Chinese herb extract and an ointment matrix, and wherein the Chinese herb extract is prepared from following raw materials in part by weight: 10-30 parts of *Sarcococca vagans* Stapf and 1-5 parts of mint.

In the present disclosure, *Sarcococca vagans* Stapf is preferably taken from roots of dried *Sarcococca vagans* Stapf. *Sarcococca vagans* Stapf, also called as *Sarcococca vagans*, belongs to *sarcococca* plants of boxwood family. No research of *Sarcococca vagans* Stapf in medicines has been reported yet. *Sarcococca vagans* Stapfs properties of diminishing inflammation and reducing swelling in the present disclosure are further explained below.

In the present disclosure, a typical but non-limited optional content of *Sarcococca vagans* Stapf is: 10 parts, 11 parts, 12 parts, 13 parts, 14 parts, 15 parts, 16 parts, 17 parts, 18 parts, 19 parts, 20 parts, 21 parts, 22 parts, 23 parts, 24 parts, 25 parts, 26 parts, 27 parts, 28 parts, 29 parts or 30 parts.

Mint is the whole herb or leaf of labiate mint, which is acrid in taste, and cool in nature, has efficacies of dispelling wind and heat, clearing head and eyes, relieving sore-throat and promoting eruption, and soothing liver and promoting the circulation of qi, and is suitable to externally contracted wind-heat, headache, swollen sore throat, dyspepsia and flatulence, aphtha, toothache, furuncle, urticaria, beginning of warm diseases, rubella pruritus, liver depression and qi stagnation, chest distress and hypochondriac pain and other diseases. Medicinal Property Theory records that "mint can eliminate anger, induce poisonous perspiration, break blood and relieve dysentery, and ease joint movement." Records of Traditional Chinese and Western Medicine in Combination records that "mint is acrid in taste, clear and sweet in fragrance, and neutral in nature. Its effect can reach muscles and bones inside, and the body surface outside, to free Zang-Fu organs, and run through meridians. Taking mint can adequately induce cold perspiration. It is an important drug for patients suffering from warm diseases and suitable to be treated by sweating."

In the present disclosure, a typical but non-limited content of the mint optionally is: 1 part, 2 parts, 3 parts, 4 parts or 5 parts.

Compatibility of the above two drugs has the efficacies of diminishing inflammation, reducing swelling, clearing heat and removing dampness.

In the present disclosure, the Chinese herb extract is preferably prepared from following raw materials in part by weight: 15-25 parts of *Sarcococca vagans* Stapf and 2-4 parts of mint.

In a preferred embodiment of the present disclosure, the Chinese herb extract is prepared from following raw materials in part by weight: 20 parts of *Sarcococca vagans* Stapf and 3 parts of mint.

By further optimizing a ratio relationship among various crude drugs, the therapeutic effect can be further improved.

The ointment matrix is used to bond various crude drugs together.

In a preferred embodiment of the present disclosure, the ointment matrix is Vaseline® petroleum jelly or polyethylene glycol.

In the present disclosure, a weight ratio of the Chinese herb extract to the ointment matrix preferably is 1:1-5, and the Chinese medicinal ointment prepared from the Chinese herb extract and the ointment matrix at different weight ratios has different viscosity and flowability.

In the present disclosure, the weight of the ointment matrix may be, typically but non-limitedly, 1 time, 2 times, 3 times, 4 times or 5 times the weight of the Chinese herb extract.

The word "include (comprise)" in the present disclosure means that apart from the components, other components further may be included, and these other components endow the Chinese medicinal ointment with different properties. Besides, the word "include (comprise)" in the present disclosure also may be replaced by close-ended "are (is)" or "consist of . . . "

The preparation method for the above Chinese medicinal ointment for treating skin disease includes following steps:

(1) preparing a Chinese herb extract, which comprises: weighing *Sarcococca vagans* Stapf and mint according to part by weight, decocting them in water, and after still standing, taking and concentrating a supernatant, to obtain the Chinese herb extract;

In the present disclosure, *Sarcococca vagans* Stapf and mint in the step (1) are preferably first cut into slices before being decocted in water, so as to immerge effective substances of the drugs in water to the greatest degree.

In the present disclosure, the amount of water added in the step (1) preferably is 12-18 times the weight of crude drugs.

In the present disclosure, the amount of the water added preferably is, typically but non-limitedly, 12 times, 13 times, 14 times, 15 times, 16 times, 17 times or 18 times the weight of the crude drugs.

In the present disclosure, the decocting preferably lasts for 30-60 minutes in the step (1).

In the present disclosure, the decocting may last for, typically but non-limitedly, 30 minutes, 35 minutes, 40 minutes, 45 minutes, 50 minutes, 55 minutes or 60 minutes.

In the present disclosure, in the step (1), after the water is added, the crude drugs are preferably decocted after being first immerged in water for 2-4 hours.

In the present disclosure, the immerging can last for, typically but non-limitedly, 2 hours, 2.5 hours, 3 hours, 3.5 hours or 4 hours.

(2) preparing an ointment, which comprises: mixing the Chinese herb extract obtained in step (1) with an ointment matrix, and stirring them evenly to prepare the ointment.

Application of the above Chinese medicinal ointment for treating skin disease, wherein the skin disease includes viral skin diseases, allergic skin diseases, fungal skin diseases and physical skin diseases.

The present disclosure further provides an application of *Sarcococca vagans* Stapf in preparation of a drug for diminishing inflammation and reducing swelling.

The technical solutions of the present disclosure are further described below in connection with Examples 1-9 and comparative examples.

In Examples 1-9, the Chinese medicinal ointment is prepared according to proportions of *Sarcococca vagans* Stapf and mint in part by weight, which is provided by the present disclosure. In the comparative example, a Chinese medicinal ointment prepared according to a different proportion of *Sarcococca vagans* Stapf and mint than those provided in the present disclosure is used.

Example 1

A preparation method for a Chinese medicinal ointment for treating skin disease provided in Example 1 is as follows:

(1) preparing a Chinese herb extract, which comprises: weighing 20 parts by weight of *Sarcococca vagans* Stapf and 3 parts by weight of mint, cutting them into slices, adding water weighing 15 times the crude drugs, decocting them for 45 minutes, and after still standing for 6 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:3, and stirring them evenly to prepare the ointment.

Example 2

A preparation method for a Chinese medicinal ointment for treating skin disease provided in Example 2 is as follows:

(1) preparing a Chinese herb extract, which comprises: weighing 25 parts by weight of *Sarcococca vagans* Stapf and 4 parts by weight of mint, cutting them into slices, adding water weighing 17 times the crude drugs, decocting them for 50 minutes, and after still standing for 7 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:4, and stirring them evenly to prepare the ointment.

Example 3

A preparation method for a Chinese medicinal ointment for treating skin disease provided in Example 3 is as follows:

(1) preparing a Chinese herb extract, which comprises: weighing 15 parts by weight of *Sarcococca vagans* Stapf and 2 parts by weight of mint, cutting them into slices, adding water weighing 16 times the crude drugs, decocting them for 40 minutes, and after still standing for 4 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:2, and stirring them evenly to prepare the ointment.

Example 4

A preparation method for a Chinese medicinal ointment for treating skin disease provided in Example 4 is as follows:

(1) preparing a Chinese herb extract, which comprises: weighing 30 parts by weight of *Sarcococca vagans* Stapf and 5 parts by weight of mint, cutting them into slices, adding water weighing 18 times the crude drugs, decocting them for 60 minutes, and after still standing for 8 hours, taking and concentrating a supernatant, to obtain the Chinese herb extract; and (2) preparing an ointment, which comprises: mixing the Chinese herb extract obtained in step (1) with polyethylene glycol according to a weight ratio of 1:5, and stirring them evenly to prepare the ointment.

Example 5

A preparation method for a Chinese medicinal ointment for treating skin disease provided in Example 5 is as follows:

(1) preparing a Chinese herb extract, which comprises: weighing 20 parts by weight of *Sarcococca vagans* Stapf and 3 parts by weight of mint, cutting them into slices, adding water weighing 15 times the crude drugs, decocting them for 45 minutes, and after still standing for 6 hours, taking and concentrating a supernatant, to obtain the Chinese herb extract; and (2) preparing an ointment, which comprises: mixing the Chinese herb extract obtained in step (1) with polyethylene glycol according to a weight ratio of 1:1, and stirring them evenly to prepare the ointment.

Example 6

A preparation method for a Chinese medicinal ointment for treating skin disease provided in Example 6 is as follows:

(1) preparing a Chinese herb extract, which comprises: weighing 10 parts by weight of *Sarcococca vagans* Stapf and 1 part by weight of mint, cutting them into slices, decocting them for 30 minutes after immersing them in water weighing 12 times the crude drugs for 2 hours, and after still standing for 4 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:2.5, and stirring them evenly to prepare the ointment.

Example 7

A preparation method for a Chinese medicinal ointment for treating skin disease provided in Example 7 is as follows:

(1) preparing a Chinese herb extract, which comprises: weighing 18 parts by weight of *Sarcococca vagans* Stapf and 2.5 part by weight of mint, cutting them into slices, decocting them for 40 minutes after immersing them in water weighing 16 times the crude drugs for 3 hours, after still standing for 5.5 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:3, and stirring them evenly to prepare the ointment.

Example 8

A preparation method for a Chinese medicinal ointment for treating skin disease provided in Example 8 is as follows:

(1) preparing a Chinese herb extract, which comprises: weighing 22 parts by weight of *Sarcococca vagans* Stapf and 3.5 parts by weight of mint, cutting them into slices, decocting them for 50 minutes after immersing them in water weighing 17.5 times the crude drugs for 5 hours, and after still standing for 6 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:3.5, and stirring them evenly to prepare the ointment.

Example 9

A preparation method for a Chinese medicinal ointment for treating skin disease provided in Example 9 is as follows:

(1) preparing a Chinese herb extract, which comprises: weighing 13 parts by weight of *Sarcococca vagans* Stapf and 1.5 parts by weight of mint, cutting them into slices, immersing them in water weighing 15.5 times the crude drugs for 2.5 hours, decocting them for 35 minutes, and after still standing for 4.5 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:1.5, and stirring them evenly to prepare the ointment.

Comparative Example

A preparation method for a Chinese medicinal ointment for treating skin disease provided in the comparative example is as follows:

(1) preparing a Chinese herb extract, which comprises: weighing 8 parts by weight of *Sarcococca vagans* Stapf and 8 parts by weight of mint, cutting them into slices, adding water weighing 15 times the crude drugs, decocting them for 45 minutes, and after still standing for 6 hours, taking and concentrating a supernatant, to obtain the Chinese herb extract; and (2) preparing an ointment, which comprises: mixing the Chinese herb extract obtained in step (1) with Vaseline® petroleum jelly according to a weight ratio of 1:3, and stirring them evenly to prepare the ointment.

Effect Example 1

For the purpose of explaining application of the Chinese medicinal ointment provided in the present disclosure for treating viral skin disease, for example, treating herpes simplex and shingles.

1. Subjects: 150 patients were collected clinically, with 82 males and 68 females, between 16 years old and 65 years old, all of whom suffered from herpes simplex or shingles.

2. Test grouping: the patients were randomly grouped into 3 groups, 50 patients in each group. The Chinese medicinal ointment prepared in Examples 1-9 was used for a test group, the Chinese medicinal ointment prepared in the comparative example was used for Control Group 1, and another commercially available ointment for treating herpes, e.g. Pi Yan Wang, was used for Control Group 2. For each patient, the corresponding ointment was applied on affected parts twice a day, for 15 days continuously.

3. Criterion of therapeutic effect:

Cured: all herpes scab or vanish, and pains disappear;

Effective: herpes substantially scab or vanish, pains are evidently relieved, and no new herpes appear;

Ineffective: herpes do not scab or vanish, pains are not relieved, and new herpes appear.

Total effective rate=(cured cases+effective cases)/ total cases

4. Clinical effects: see Table 1 for therapeutic effects to viral skin diseases in each group.

TABLE 1

Therapeutic Effects to Viral Skin Diseases in Each Group

| Group | Total Cases | Cured | Effective | Ineffective | Total Effective Rate |
|---|---|---|---|---|---|
| Test Group | 50 | 48 | 2 | 0 | 100% |
| Control Group 1 | 50 | 10 | 26 | 14 | 72% |
| Control Group 2 | 50 | 17 | 22 | 11 | 78% |

It can be seen from Table 1 that the Chinese medicinal ointment of the present disclosure has good curative effect to viral skin diseases, such as shingles, with an effective rate of up to 100%, far higher than that of commercially available ointment for treating skin diseases provided in Control Group 2, and reduces patients' pains. Meanwhile, the effective rate of Control Group 1 is far lower than that of the test group, which indicates that compatibility of raw materials of a Chinese medicine combination plays a crucial role for exerting the pharmaceutical effect, and if the compatibility cannot meet requirements, ideal therapeutic effects cannot be reached, thus affecting the patients' recovery.

Effect Example 2

For the purpose of explaining application of the Chinese medicinal ointment provided in the present disclosure for treating allergic skin diseases, for example, treating dermatitis and eczema.

1. Subjects: 300 patients were collected clinically, with 159 males and 131 females, between 19 years old and 68 years old, all of whom suffered from allergic dermatitis.

2. Test grouping: the patients were randomly grouped into 3 groups, 100 patients in each group. The Chinese medicinal ointment prepared in Examples 1-9 was used for the test group, the Chinese medicinal ointment prepared in the comparative example was used for Control Group 1, and another commercially available ointment for treating dermatitis, e.g. Fluocinolone acetonide, was used for Control Group 2. For each patient, the corresponding ointment was applied on affected parts twice a day, for 1 month continuously.

3. Criterion of therapeutic effect:
Cured: clinical symptoms completely disappear;
Effective: clinical symptoms are evidently improved;
Ineffective: clinical symptoms are not evidently improved or aggravated.

Total effective rate=(cured cases+effective cases)/total cases

4. Clinical effects: see Table 2 for therapeutic effects to allergic skin diseases in each group.

TABLE 2

Therapeutic Effects to Allergic Skin Diseases in Each Group

| Group | Total Cases | Cured | Effective | Ineffective | Total Effective Rate |
|---|---|---|---|---|---|
| Test Group | 100 | 89 | 10 | 1 | 99% |
| Control Group 1 | 100 | 16 | 39 | 45 | 55% |
| Control Group 2 | 100 | 40 | 37 | 23 | 77% |

It can be seen from Table 2 that the Chinese medicinal ointment of the present disclosure has good curative effect to allergic skin diseases, such as allergic dermatitis, with an effective rate of up to 99%, far higher than that of commercially available ointment for treating skin diseases provided in Control Group 2, and reduces patients' pains. Meanwhile, the effective rate of Control Group 1 is far lower than that of the test group, which indicates that compatibility of raw materials of a Chinese medicine combination plays a crucial role for exerting the pharmaceutical effect, and if the compatibility cannot meet requirements, ideal therapeutic effects cannot be reached, thus affecting the patients' recovery.

Effect Example 3

For the purpose of explaining application of the Chinese medicinal ointment provided in the present disclosure for treating fungal skin diseases, for example, treating tinea capitis, tinea corporis, tinea cruris and tinea of feet and hands.

1. Subjects: 150 patients were collected clinically, with 101 males and 49 females, between 16 years old and 65 years old, all of whom suffered from tinea capitis, tinea corporis, tinea cruris or tinea of feet and hands.

2. Test grouping: the patients were randomly grouped into 3 groups, 50 patients in each group. The Chinese medicinal ointment prepared in Examples 1-9 was used for the test group, the Chinese medicinal ointment prepared in the comparative example was used for Control Group 1, and another commercially available ointment for treating tinea corporis, e.g. Ketoconazole, was used for Control Group 2. For each patient, the corresponding ointment was applied on affected parts twice a day, for 2 months continuously.

3. Criterion of therapeutic effect:
Cured: Fungi microscopic examination is negative, and tinea and pruritus completely disappear;
Effective: Fungi microscopic examination is negative, tinea substantially disappears, and pruritus is evidently alleviated;
Ineffective: Fungi microscopic examination is positive, and tinea and pruritus are not relieved.

Total effective rate=(cured cases+effective cases)/total cases

4. Clinical effects: see Table 3 for therapeutic effects to fungal skin diseases.

TABLE 3

Therapeutic Effects to Fungal Skin Diseases

| Group | Total Cases | Cured | Effective | Ineffective | Total Effective Rate |
|---|---|---|---|---|---|
| Test Group | 50 | 45 | 5 | 0 | 100% |
| Control Group 1 | 50 | 12 | 20 | 18 | 64% |
| Control Group 2 | 50 | 16 | 21 | 13 | 74% |

It can be seen from Table 3 that the Chinese medicinal ointment of the present disclosure has good curative effect to the fungal skin diseases, such as tinea capitis, tinea corporis, tinea cruris and tinea of feet and hands, with an effective rate of up to 100%, far higher than that of commercially available ointment for treating skin diseases provided in Control Group 2, and reduces patients' pains. Meanwhile, the effective rate of Control Group 1 is far lower than that of the test group, which indicates that compatibility of raw materials of a Chinese medicine combination plays a crucial role for exerting the pharmaceutical effect, and if the compatibility cannot meet requirements, ideal therapeutic effects cannot be reached, thus affecting the patients' recovery.

Effect Example 4

For the purpose of explaining application of the Chinese medicinal ointment provided in the present disclosure for treating physical skin diseases, for example, treating frostbite.

1. Subjects: 150 patients were collected clinically, with 57 males and 93 females, between 15 years old and 65 years old, all of whom suffered from frostbite.

2. Test grouping: the patients were randomly grouped into 3 groups, 50 patients in each group. The Chinese medicinal ointment prepared in Examples 1-9 was used for the test group, the Chinese medicinal ointment prepared in the comparative example was used for Control Group 1, and another commercially available ointment for treating frostbite, e.g. anti-cracking and freeze-proofing snake oil ointment, was used for Control Group 2. For each patient, the corresponding ointment was applied on affected parts twice a day, for 5 days continuously.

3. Criterion of therapeutic effect:

Cured: symptoms disappear, lumps vanish, and wound surfaces heal;

Effective: symptoms are evidently improved, and wound surfaces substantially heal;

Ineffective: symptoms are not evidently improved.

Total effective rate=(cured cases+effective cases)/total cases

4. Clinical effects: see Table 4 for therapeutic effects to frostbite in each group.

TABLE 4

Therapeutic Effects to Frostbite in Each Group

| Group | Total Cases | Cured | Effective | Ineffective | Total Effective Rate |
|---|---|---|---|---|---|
| Test Group | 50 | 47 | 3 | 0 | 100% |
| Control Group 1 | 50 | 14 | 17 | 19 | 62% |
| Control Group 2 | 50 | 19 | 16 | 15 | 70% |

It can be seen from Table 4 that the Chinese medicinal ointment of the present disclosure has good curative effect to frostbite, with an effective rate of up to 100%, far higher than that of commercially available ointment for treating frostbite provided in Control Group 2, and reduces patients' pains. Meanwhile, the effective rate of Control Group 1 is far lower than that of the test group, which indicates that compatibility of raw materials of a Chinese medicine combination plays a crucial role for exerting the pharmaceutical effect, and if the compatibility cannot meet requirements, ideal therapeutic effects cannot be reached, thus affecting the patients' recovery.

Effect Example 5

For the purpose of explaining application of the Chinese medicinal ointment provided in the present disclosure for treating physical skin diseases, for example, treating burn and scald.

1. Subjects: 150 patients were collected clinically, with 84 males and 66 females, between 15 years old and 60 years old, all of whom suffered from burn and scald, superficial II degree for 96 cases, and deep II degree for 54 cases.

2. Test grouping: the patients were randomly grouped into 3 groups, 50 patients in each group. The Chinese medicinal ointment prepared in Examples 1-9 was used for the test group, the Chinese medicinal ointment prepared in the comparative example was used for Control Group 1, and another commercially available ointment for treating burn and scald, e.g. Hua Tuo Burn and Scald Cream, was used for Control Group 2. For patients of superficial II degree, the corresponding ointment was applied once a day, continuously for 7 days; for patients of deep II degree, the corresponding ointment was applied twice a day, continuously for 15 days.

3. Criterion of therapeutic effect:

Cured: pains, and red and swollen disappear, and there is no evident scar;

Effective: pains, and red and swollen are alleviated, and there is slight scar;

Ineffective: pains, and red and swollen are not alleviated, and there is evident scar.

Total effective rate=(cured cases+effective cases)/total cases

4. Clinical effects: see Table 5 for therapeutic effects to burn and scald in each group.

TABLE 5

Therapeutic Effects to Burn and Scald in Each Group

| Group | Total Cases | Cured | Effective | Ineffective | Total Effective Rate |
|---|---|---|---|---|---|
| Test Group | 50 | 45 | 5 | 0 | 100% |
| Control Group 1 | 50 | 10 | 17 | 23 | 54% |
| Control Group 2 | 50 | 14 | 16 | 20 | 60% |

It can be seen from Table 5 that the Chinese medicinal ointment of the present disclosure has good curative effect to burn and scald, with an effective rate of up to 100%, far higher than that of commercially available ointment for treating burn and scald provided in Control Group 2, and reduces patients' pains. Meanwhile, the effective rate of Control Group 1 is far lower than that of the test group, which indicates that compatibility of raw materials of a Chinese medicine combination plays a crucial role for exerting the pharmaceutical effect, and if the compatibility cannot meet requirements, ideal therapeutic effects cannot be reached, thus affecting the patients' recovery.

Efficacies of *Sarcococca vagans* Stapf of the present disclosure are tested and researched below.

Effect Example 6

Influences of *Sarcococca vagans* Stapf to xylene-induced mouse ear edema.

Roots of *Sarcococca vagans* Stapf were dried in the sun, and ground to powder for subsequent use.

1. Test animals: healthy, qualified and clean Kunming mice, half females and half males, with a body weight of 18-22 g, which were provided by Chongqing Medical University Test Animal Center, with certificate Medical Animal Zi No. 14301041.

2. Test reagent: *Sarcococca vagans* Stapf powder, dexamethasone acetate tablets (Zhejiang Xianju Pharmaceutical Co., Ltd., batch No. 120347), and glacial acetic acid and xylene were both analytically pure.

3. Test method: 50 test mice were randomly divided into 5 groups, 10 mice in each group, and the groups respectively were normal control group, dexamethasone group, high-dosage *Sarcococca vagans* Stapf powder group, medium-dosage *Sarcococca vagans* Stapf powder group, and low-dosage *Sarcococca vagans* Stapf powder group.

After the *Sarcococca vagans* Stapf powder was sieved by 120 meshes, a suitable amount of the *Sarcococca vagans* Stapf powder was taken and dissolved in a 0.5% sodium carboxymethylcellulose solution, to prepare high-dosage (0.30 g/ml), medium-dosage (0.15 g/ml), and low-dosage (0.075 g/ml) *Sarcococca vagans* Stapf powder suspension. The dexamethasone acetate tablets were ground in the 0.5% sodium carboxymethylcellulose solution, to prepare 19.8 ug/ml suspension.

The normal group was fed with the 0.5% sodium carboxymethylcellulose solution; the dexamethasone group was fed with the dexamethasone solution at 9.9 ug/kg (equivalent to 20 times human usage amount); the high-dosage (15 g/kg), medium-dosage (7.5 g/kg), and low-dosage (3.75 g/kg) groups were respectively fed with the *Sarcococca vagans* Stapf powder suspension according to corresponding dosages.

For each group, the mice were fed twice each day for first two days, once on the third day, and after 30 min, 0.05 ml of xylene was applied to both front and back faces of right ear of each mouse in each group, while left ear was not coated with the medicine as control. 40 min after the coating, the mice were killed by cervical dislocation, the left and right ears were cut off, and ear slices at the same parts of the two ears were taken with a puncher and weighed. The difference between weights of the left and right ears is swelling degree. Each group was recorded, and t test was carried out among the groups. A swelling inhibition rate of the tested medicines was calculated according to a following formula: swelling inhibition rate=(mean swelling degree of the normal group−mean swelling degree of the administration group)/mean swelling degree of the normal group× 100%.

See Table 6 for influences of *Sarcococca vagans* Stapf to xylene-induced mouse ear edema.

TABLE 6

Influences of *Sarcococca Vagans Stapf* to Xylene-induced Mouse Ear Edema

| Group | Swelling Degree (g) | Swelling Inhibition Rate % |
|---|---|---|
| High-dosage Group | 0.0055 ± 0.0022 | 56.3Δ |
| Medium-dosage Group | 0.0063 ± 0.0042 | 50.1Δ |
| Low-dosage Group | 0.0081 ± 0.0028 | 36.1Δ |
| Dexamethasone Group | 0.0101 ± 0.0034 | 20.0 |
| Normal Group | 0.0127 ± 0.0041 | |

Notes:
compared with the normal group, ΔP < 0.05.

It can be seen from Table 6 that *Sarcococca vagans* Stapf, within the range of the tested dosage, has evident inhibition effect on the xylene-induced mouse ear edema, and its effect is also superior to the dexamethasone group, indicating that *Sarcococca vagans* Stapf has certain effects of diminishing inflammation and reducing swelling.

Effect Example 7

Test for *Sarcococca vagans* Stapfs effect of inhibiting capillary permeability.

Roots of *Sarcococca vagans* Stapf were dried in the sun, and ground to powder for subsequent use.

1. Test animals: healthy, qualified and clean Kunming mice, half females and half males, with a body weight of 18-22 g, which were provided by Chongqing Medical University Test Animal Center, with certificate Medical Animal Zi No. 14301041.

2. Test reagent: *Sarcococca vagans* Stapf powder, dexamethasone acetate tablets (Zhejiang Xianju Pharmaceutical Co., Ltd., batch No. 120347), and glacial acetic acid and xylene were both analytically pure.

3. Test method: 50 test mice were randomly divided into 5 groups, 10 mice in each group, and the groups respectively were normal control group, dexamethasone group, high-dosage *Sarcococca vagans* Stapf powder group, medium-dosage *Sarcococca vagans* Stapf powder group, and low-dosage *Sarcococca vagans* Stapf powder group.

After the *Sarcococca vagans* Stapf powder was sieved by 120 meshes, a suitable amount of the *Sarcococca vagans* Stapf powder was taken and dissolved in a 0.5% sodium carboxymethylcellulose solution, to prepare high-dosage (0.30 g/ml), medium-dosage (0.15 g/ml), and low-dosage (0.075 g/ml) *Sarcococca vagans* Stapf powder suspension. The dexamethasone acetate tablets were ground in the 0.5% sodium carboxymethylcellulose solution, to prepare 19.8 ug/ml suspension.

The normal group was fed with the 0.5% sodium carboxymethylcellulose solution; the dexamethasone group was fed with the dexamethasone solution at 9.9 ug/kg (equivalent to 20 times human usage amount); the high-dosage (15 g/kg), medium-dosage (7.5 g/kg), and low-dosage (3.75 g/kg) groups were respectively fed with the *Sarcococca vagans* Stapf powder suspension according to corresponding dosages.

For each group, the mice were fed twice each day for the first two days, fed once on the third day, after 30 min, the animals in each group were injected with Evans blue saline at 0.1 ml/10 g through tail vein, then were intraperitoneally injected with 0.9% glacial acetic acid, 40 min after the injection, each animal was killed by cervical dislocation, whose abdominal cavity was washed with saline, and a washing liquid was collected, to be adjusted to a volume of 7 ml, centrifuged at 3000 r/min for 5 min, and measured in absorbance at a 580 nm wavelength.

See Table 7 for *Sarcococca vagans* Stapf powder's effect of inhibiting capillary permeability of mouse abdominal cavities.

TABLE 7

*Sarcococca Vagans Stapf* Powder's Effect of Inhibiting Capillary Permeability

| Group | Absorbance (A) |
|---|---|
| High-dosage Group | 0.294 ± 0.029Δ |
| Medium-dosage Group | 0.415 ± 0.224Δ |
| Low-dosage Group | 0.509 ± 0.104Δ |
| Dexamethasone Group | 0.569 ± 0.238 |
| Normal Group | 0.832 ± 0.387 |

Notes:
compared with the normal group, ΔP < 0.05.

It can be seen from Table 7 that the absorbance of the groups using *Sarcococca vagans* Stapf powder is far lower than that of the normal group, and is also lower than the dexamethasone group, it thus can be seen that *Sarcococca vagans* Stapf can resist inflammation-caused capillary permeability increase of the mouse skin.

It can be seen from Effect Example 5 and Effect Example 6 that *Sarcococca vagans* Stapf has the efficacies of diminishing inflammation and reducing swelling.

The effects of the present disclosure are further described below by listing several typical cases:

Typical Case 1

Chen, male, 45 years, suffered from shingles for 3 years, with densely-distributed shingles having a soybean size on back and waist, and felt intolerably painful, weak all over, and uneasy even when eating and sleeping. He had used some ointments but the curative effect was unfavorable, after that, he used the Chinese medicinal ointment provided in Example 3 of the present disclosure, three times a day, and the pains were relieved that day. After 3 days the pains disappeared, the herpes began to scab or vanish. He was substantially cured after 10 days. No relapse was found in half-a-year follow-up.

Typical Case 2

Zhang, male, 36 years, suffered from eczema for 5 years. At the beginning, eczema was found at one place of shoulders, and gradually developed to lumps and masses. Two months later, the eczema covered the whole shoulder portions and the back, the red eczema spread all over the upper body, accompanied by excruciating itching, making him uneasy even when eating and sleeping. He sought medicines all around but was not cured. After that, he used the Chinese medicinal ointment provided in Example 1 of the present disclosure, three times a day. After 1 month of treatment, an area of the eczema was gradually reduced locally, and symptoms were alleviated. After the treatment was continued for 5 months, he was substantially restored. No relapse was found in one-year follow-up.

Typical Case 3

Ji, female, 52 years, suffered from tinea for years. At the beginning, erythema and blisters appeared on part of the skin of left hand. After the blisters burst, desquamation phenomenon appeared at affected parts, accompanied by scratchiness, and gradually spread around, then the same symptom occurred also to right hand, and gradually tinea appeared on the whole body. After using the Chinese medicinal ointment provided in Example 2 of the present disclosure, three times a day, for 1 month of treatment, an area of the tinea corporis was gradually reduced locally, and symptoms, such as scratchiness, were evidently alleviated. After the treatment was continued for 2 months, he was restored. Fungi microscopic examination was negative. No relapse was found in one-year follow-up.

Typical Case 4

Li, female, 47 years, suffered from frostbite at hands and face every winter, with edematous skin, erythema, and pains. After using the Chinese medicinal ointment provided in Example 5 of the present disclosure, four times a day, for 5 days, the symptoms were evidently relieved. After 10 days, she was cured. In the next winter, she continued to use the present Chinese medicinal ointment, and no frostbite occurred again. No relapse was found in 2-year follow-up.

Typical Case 5

Zhang, male, 60 years, stayed in bed over a long period of time due to physical illness, causing ischemic necrosis of hips, ulcer and erosion, and having purulent secretion. After using the Chinese medicinal ointment provided in Example 4 of the present disclosure, three times a day, for 10 days, pus and blood secretion was gradually reduced, afterwards, new flesh gradually grew out, and after 1 month, wound surfaces were cured, and no evident scar was formed.

Typical Case 6

Wei, female, 39 years, was seriously burnt at two hands and arms due to gas fire, deep II degree burn. After treated in hospital for several days, and injected with antibiotics through veins, the curative effect was unfavorable, the two hands and the arms swelled, wound surfaces were black, with dry and hard scabs, and infection and purulency under scabs, and the pains were intolerable. She used the Chinese medicinal ointment provided in Example 2 twice a day, and at the same day, the pains were alleviated, scabs were softened and started to fall off. After 3 days, the scabs came off, and a lot of purulent wound surfaces were exposed. After cleaning, the Chinese medicinal ointment of the present disclosure was applied continuously, and new flesh gradually grew out. After 2 weeks, the patient was cured, with red skin, and no scar was formed.

Typical Case 7

Chen, male, 30 years, suffered from allergic dematitis, with flushing plaques at head, and gray canicaceous scales thereon, accompanied by itching, particularly affecting nighttime sleep. After using the Chinese medicinal ointment provided in Example 3, one time a day, for 3 days, itching was evidently alleviated, and after continuous use of the medicine for 15 days, the symptoms completely disappeared. No relapse was found in 5-month follow-up.

Finally, it should be explained that the various embodiments above are merely used for illustrating the technical solutions of the present disclosure, rather than limiting the present disclosure. Although the detailed description is made to the present disclosure with reference to various preceding examples, those ordinarily skilled in the art should understand that they still could modify the technical solutions recited in various preceding examples, or make equivalent substitutions to some or all of the technical features therein. These modifications or substitutions do not make the corresponding technical solutions essentially depart from the scope of the technical solutions of the various examples of the present disclosure.

What is claimed is:

1. A method for treating skin diseases, comprising administering a therapeutically effective amount of an ointment, wherein the ointment consists of an herb extract and an ointment matrix, and wherein the herb extract is prepared from the following raw materials in parts by weight: 10-30 parts of *Sarcococca vagans* Stapf and 1-5 parts of mint.

2. The method according to claim 1, wherein the herb extract is prepared from the following raw materials in parts by weight: 12-28 parts of the *Sarcococca vagans* Stapf and 2-4 parts of the mint.

3. The method according to claim 1, wherein the herb extract is prepared from the following raw materials in parts by weight: 15-25 parts of the *Sarcococca vagans* Stapf and 2-4 parts of the mint.

4. The method according to claim 1, wherein the herb extract is prepared from the following raw materials in parts by weight: 15 parts of the *Sarcococca vagans* Stapf and 2 parts of the mint.

5. The method according to claim 1, wherein the herb extract is prepared from the following raw materials in parts by weight: 20 parts of the *Sarcococca vagans* Stapf and 3 parts of the mint.

6. The method according to claim 1, wherein the herb extract is prepared from the following raw materials in parts by weight: 30 parts of the *Sarcococca vagans* Stapf and 5 parts of the mint.

7. The method according to claim 1, wherein the *Sarcococca vagans* Stapf is roots of dried *Sarcococca vagans* Stapf.

8. The method according to claim 1, wherein the ointment matrix is Vaseline® petroleum jelly or polyethylene glycol.

9. The method according to claim 1, wherein a weight ratio of the herb extract to the ointment matrix is 1:1-5.

10. The method according to claim 1, wherein the skin diseases comprise viral skin diseases, allergic skin diseases, fungal skin diseases and physical skin diseases.

11. The method according to claim 2, wherein the herb extract is prepared from the following raw materials in parts by weight: 15-25 parts of the *Sarcococca vagans* Stapf and 2-4 parts of the mint.

12. The method according to claim 2, wherein the *Sarcococca vagans* Stapf is roots of dried *Sarcococca vagans* Stapf.

13. The method according to claim 2, wherein the ointment matrix is Vaseline® petroleum jelly or polyethylene glycol.

14. The method according to claim 2, wherein a weight ratio of the herb extract to the ointment matrix is 1:1-5.

* * * * *